(12) United States Patent
Hammond et al.

(10) Patent No.: US 8,492,444 B2
(45) Date of Patent: Jul. 23, 2013

(54) BIOGENIC SILICA FROM SILICA-CONTAINING PLANT MATERIAL SUCH AS RICE HULLS

(76) Inventors: Neal A. Hammond, Phoenix, AZ (US); J. Steve Peirce, St. Louis, MO (US)

( * ) Notice: Subject to any disclaimer, the term of this patent is extended or adjusted under 35 U.S.C. 154(b) by 1079 days.

(21) Appl. No.: 12/375,967

(22) Filed: Feb. 2, 2009

(65) Prior Publication Data

US 2012/0041081 A1 Feb. 16, 2012

Related U.S. Application Data

(63) Continuation of application No. PCT/US2007/017304, filed on Aug. 2, 2007.

(60) Provisional application No. 60/835,062, filed on Aug. 2, 2006.

(51) Int. Cl.
*A01N 25/00* (2006.01)
*A61K 47/00* (2006.01)

(52) U.S. Cl.
USPC .......... 514/783; 435/267; 426/442; 426/518; 426/52; 426/248

(58) Field of Classification Search
None
See application file for complete search history.

(56) References Cited

U.S. PATENT DOCUMENTS

| | | | |
|---|---|---|---|
| 3,767,423 A | 10/1973 | Tsantir | |
| 4,049,464 A | 9/1977 | Tutsek | |
| 4,407,789 A | 10/1983 | Eigen | |
| 4,571,389 A | 2/1986 | Goodwin | |
| 4,619,911 A | 10/1986 | Goodwin | |
| 4,727,824 A | 3/1988 | Ducharme | |
| 4,735,808 A * | 4/1988 | Scaglione et al. | 426/62 |
| 5,688,448 A | 11/1997 | Shutov | |
| 6,290,933 B1 * | 9/2001 | Durga et al. | 424/49 |
| 6,352,210 B1 | 3/2002 | Requejo | |
| 6,406,678 B1 | 6/2002 | Shipley | |
| 6,436,431 B1 | 8/2002 | Hoffpauer | |
| 6,444,186 B1 | 9/2002 | Vempati | |
| 6,843,974 B2 | 1/2005 | Kang | |
| 2003/0203058 A1 | 10/2003 | Cheruvanky | |
| 2005/0260326 A1 | 11/2005 | Kageyama | |
| 2007/0154412 A1 * | 7/2007 | Phillips et al. | 424/58 |

FOREIGN PATENT DOCUMENTS

| | | |
|---|---|---|
| EP | 0079707 A | 5/1983 |
| KR | 2002 0090661 A | 12/2002 |
| WO | WO 02/06157 A | 1/2002 |
| WO | WO 2007/078651 A | 7/2007 |

OTHER PUBLICATIONS

Towatana et al, Environmental Geochemistry and Health 25: 365-386, 2003.*
Database FSTA [online] International Food Information Service (IFIS) Frankfurt-Main, DE: Adrians R et al: "Wheat fiber—a natural food ingredient." XP002467161 Database accession No. 95-1-07-m0068.
Database BIOSIS [online] Biosciences Information Service, Philadelphia, PA, US: 1992, Siri S et al: "Effects of dietary fibers on growth performance development of internal organs protein and energy utilization and lipid content of growing chicks." XP002467162 Database accession No. PREV 199294044490.
International Silica Technologies, LLC: "StratoSil (TM)" [online] XP002467169 Retrieved from the Internet: URL:http://www.dakram.com/09-StratoSil-Website-Home-Page-5-19-04.pdf [retrieved on Jan. 30, 2008].
International Search Report and Written Opinion from PCT application No. PCT/US2007/017304.

* cited by examiner

*Primary Examiner* — Brandon Fetterolf
*Assistant Examiner* — Jean Cornet
(74) *Attorney, Agent, or Firm* — Grace J. Fishel

(57) ABSTRACT

A biogenic silica from a plant material such as rice hulls, rice straw and so forth containing a significant amount of silica for use as an anti-caking agent, excipient or flavor carrier. When the plant material is certified as organic, the silica may also be certified as organic. The plant material is ground and the silica may be concentrated by carbon reduction through enzymatic treatment or burning. In some instances an antimicrobial treatment of the silica may be beneficial.

4 Claims, 2 Drawing Sheets

US 8,492,444 B2

BIOGENIC SILICA FROM SILICA-CONTAINING PLANT MATERIAL SUCH AS RICE HULLS

This application is a continuation of PCT/US2007/017304, filed Aug. 2, 2007 which claimed priority from U.S. provisional application 60/835,062, filed Aug. 2, 2006.

BACKGROUND OF THE INVENTION

1. Field of the Invention

The present invention relates to biogenic amorphous silica isolated from a plant material containing silica such as rice hulls, rice straw and so forth.

2. Brief Description of the Prior Art

Silica (silicon dioxide) occurs in crystalline and amorphous forms. Large quantities of synthetic amorphous silica are produced as pyrogenic (fumed) silicas and wet process silicas (precipitated silicas and silica gels) which are used, notably, for reinforcing elastomers, for thickening resins, paints and toothpaste, and as free-flow additives. Synthetic amorphous silica may also be ingested as a minor constituent (<2%) in a variety of food products where it serves as an anti-caking agent. Amorphous silica is also used in some pharmaceutical preparations for the same purposes.

Amorphous silica is found in nature as biogenic silica and as silica glass of volcanic origin. One form of biogenic silica, originates from the skeletons of diatoms deposited on sea floors but it contains a small amount of cristobalite (a crystalline form of silica) and quartz (another crystalline form of silica). Most producers of food and pharmaceutical products require that the amorphous silica used as an anti-caking agent contain no detectable amount of crystalline silica.

It is known that fibers of amorphous silica are produced by a variety of plants, such as sugar cane and rice. Of known plant materials, however, the rice plant is perhaps unique because of the high concentrations of silica that it contains. Whereas, the mineral content of most plants is, for example, about 1-2%, the rice plant typically has a mineral content of about 11-23%. More importantly, about 75-95% of the mineral content of the rice plant is silica. Of the rice plant, rice straw contains about 11% silica and rice hulls typically contain about 15-23% silica.

Rice hulls are the natural sheaths that form on rice grains during their growth. They are removed during the refining of rice and are a waste or a low-value by-product of the rice milling industry. Rice straw consists of stem, leaf sheathes, leaf blades and the remains of the panicle after harvesting. Generally, the amount of rice straw obtained from rice plants is at least equal to the rough yield of rice harvested. Because of their high silica content, rice hulls and rice straw have little value as components of animal feeds. Also, because these materials have a relatively large amount of potassium that interacts with the silica at combustion temperatures to produce boiler slag and deposits, and have a large fraction of noncombustible ash, they are similarly viewed as being a poor fuel source. For these reasons, rice hulls are frequently deposited in landfills and rice straw is usually burned in the fields. Thus rice hulls and rice straw have little or no commercial value and have historically presented a disposal problem.

Recent U.S. legislation has prohibited the use of synthetics (e.g., amorphous silicas such as fumed silica) in products which are marketed as organic foods. Currently there is an exemption to this law for synthetic silica because there is no biogenic silica. The present invention provides a source of biogenic silica that can be certified as organic.

BRIEF SUMMARY OF THE INVENTION

In view of the above, it is an object of the present invention to provide a biogenic source of amorphous silica from a plant material containing at least three weight percent of silica and preferably more than ten percent. It is another object to provide a source of silica from a plant material such as rice hulls or rice straw which may be certified as organic. It is also an object to provide a biogenic silica for use as an anti-caking agent, excipient or flavor carrier in foods, drinks, supplements, personal care products and pharmaceuticals. Other objects and features of the invention will be in part apparent and in part pointed out hereinafter.

In accordance with the invention, an anti-caking agent, excipient or carrier is formed from a plant material such as rice hulls, rice straw or other such plant material that contains at least 3% and preferably more than 10% of silica and most preferably more than 20% by weight of silica. When the plant material is certified as organic, the anti-caking agent, excipient or flavor carrier may also be certified as organic.

For use as an anti-caking agent, excipient or flavor carrier, the plant material such as rice hulls are milled into a desired particle size and compounded with the host material. The silica content of the anti-caking agent, excipient or flavor carrier may be concentrated by reducing the organic content of the rice hulls by treatment with enzymes or by burning. If desired, the silica extracted from the rice hulls may be converted into a crystalline form which may potentially be certified as "organic."

The invention summarized above comprises the methods and formulations hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding elements throughout the several views of the drawings in which.

DETAILED DESCRIPTION OF THE INVENTION

Figure 1:
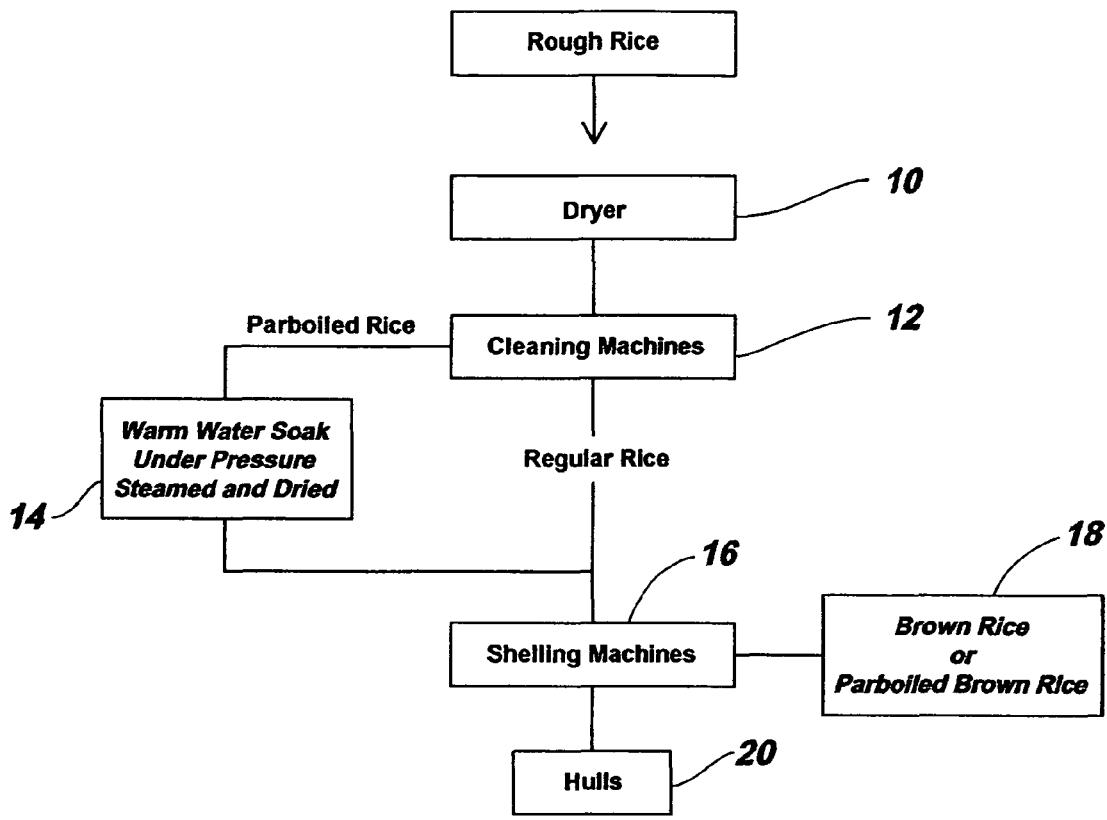
FIG. 1 is a schematic process diagram showing conversion of rough rice into brown rice or parboiled brown rice and rice hulls in a conventional manner.

Referring first to FIG. 1, a source of a plant material containing silica such as rough rice, also known as paddy rice, is dried 10 to a suitable moisture level and rice straw, weed seeds and other field debris are removed by a series of cleaning machines 12 prior to milling. The dried rough rice may be parboiled with a warm water soak under pressure, steamed and dried 14 before it is dehulled. The outer hulls of the rice grain are removed by shelling machines 16 and brown rice or parboiled rice 18 is separated from hulls 20.

In the present invention, rice hulls 20 are processed as described hereinafter into a form suitable for use in a human or animal food, drink, supplement, personal care or pharmaceutical product as an anti-caking agent, excipient or flavor carrier. As an anti-caking agent, the rice hull products are blended with a finely divided or powdered host material to improve its flowability. Alternatively, the product and rice hulls 20 may also be co-sprayed or co-ground together at an earlier stage in the treatment of the rice hulls as described below. The anti-caking effect may be the result of a physical separation of the host particles, inhibition of interparticle interactions, lubrication, competition for water absorption, cancellation of electrostatic forces, etc. The term excipient refers to use as an inert ingredient added to a food, drink, supplement, personal care or pharmaceutical product to give a desired consistency or form. The term carrier refers to a material onto which a food, drink, supplement, personal care or pharmaceutical product is plated or otherwise adhered. A flavor carrier may be used to obtain a uniform blend of a small or trace amount of material into a larger batch of host particles.

As mentioned above, rice hulls 20 are known to contain about 15-23% by weight of silica. The silica is in amorphous form and is located in the outer layers of the husk. Synthetic amorphous silica is commonly used as an inert anti-caking agent in food and pharmaceutical products. For use in the present invention, ground rice hulls and biogenic amorphous silica isolated from rice hulls is used in an effective amount as an anti-caking agent, excipient or flavor carrier. When the rough rice is certified as organic, rice hulls 20 and the silica contained therein may be certified as organic and thus suitable for use in organic human food, personal care formulations and animal feed. The usage level may be the same as the usage level of synthetic amorphous silicas. However, larger quantities may be required to compensate for the lower concentration of silica as compared to fumed silicas.

Figure 2:
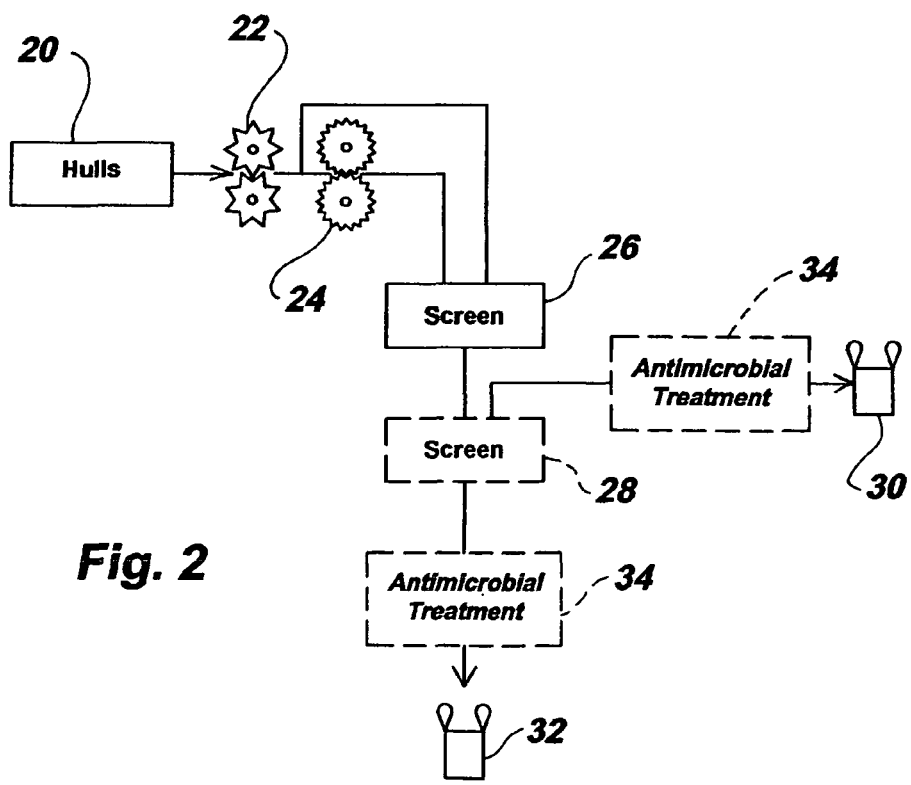
FIG. 2 is a schematic process diagram showing conversion of rice hulls into ground rice hulls for use as an anti-caking agent, excipient or flavor carrier in accordance with the present invention.

Referring now to FIG. 2, a plant material such as rice hulls 20 as they emerge from shelling machine 16 are ground into a finely divided state. When the plant material is rice hulls, the hulls may be milled to particle sizes ranging from about 10 microns or less to about 1,500 microns. The size of the particles and particle size distribution is application dependent. Grinding may occur in a single or multiple stages.

As illustrated in FIG. 2, a first stage of grinding of a plant material such as rice hulls 20 occurs in a hammermill 22 followed by a second stage of finer grinding in a pulverizer 24. The ground rice hulls may then be screened to obtain the desired particle size for the product. A two-stage screening is shown in FIG. 2 wherein, for illustration purposes only, particles less than 75 microns pass through screen 26 and particles less than 45 microns pass through screen 28. The oversize particles which do not pass through screen 26 may be recycled through pulverizer 24 for further grinding. The particles passing through first screen 26 but not through second screen 28 may be packaged as a first product 30 while the particles passing through second screen 28 may be packaged as a second product 32 having smaller particles. As described above, products 30, 32 may be used as an anti-caking agent, excipient or flavor carrier in food, drink, supplement, personal care or pharmaceutical products. If rice hulls 20 come from rice certified as organic, the ground rice hull products 30, 32 may also be certified as organic.

Before packaging, an antimicrobial treatment 34 may be applied to products 30, 32 to reduce the microbial count to an acceptable level. Suitable treatments may include pasteurization, gasification, irradiation or the like. Gasification may be with carbon dioxide, ethylene oxide, ozone or other approved materials to achieve the desired results and ultraviolet light or electrons may be used. The particular antimicrobial treatment 34 selected may depend upon the intended end use for the ground rice hulls and be determined by organic or customer standards. For example, if the intended use of the ground rice hulls is in certified organic food products in the USA, then irradiation or ethylene treatment are not permitted under current USDA regulations.

The functionality of the ground rice hulls processed as described above may be enhanced by proper matching of their moisture level to the product or by grinding the rice hulls into smaller particles and matching them as an anti-caking agent to the product. For example, hygroscopic products such as honey, dried fruit, apples, pears, enzymes, etc. and items dried to very low moisture (e.g., 2-3% by weight) are best paired with ground rice hulls that are dried to a low moisture level. Ground rice hulls with a higher moisture content (e.g., 8-10%) used with hygroscopic products and items dried to a low moisture content initially act as an anti-caking agent but over time put moisture into the product and may cause caking.

Drying of the ground rice hulls and microbial treatment may be achieved at the same time. For example when the ground rice hulls are dried under UV light to a moisture level of 2-3%, there is a coinciding reduction in the microbial level. For use in some products, reduction of the microbial level extends the application range for the ground rice hulls. Treatment of the ground rice hulls in an impingement oven has produced similar effects.

Grinding the subject rice hulls into smaller particles also effects functionality. When the rice hulls are ground in a ball mill, it is possible to achieve particle sizes in the range of 7 to 20 microns. Other mills, however, may be able to reduce the particle size to below 1 micron. At some level of reduction, the ground rice hulls, which are usually viewed as an insoluble, become soluble or suspendable in water thus extending the range of applications in beverages, nutrition drinks, etc. and allowing the formulation of "hypoallergenic/ organic fiber" into a beverage. In alcohol, finely ground rice hulls may be placed in suspension to form a gel. Suspension of the ground rice hulls in an alcohol may change the properties of the ground rice hulls and enhance their solubility or suspendability in water, further extending applications in beverage or food products, for example.

Other properties of the ground rice hulls open additional application possibilities. For example, the ground rice hulls are capable of absorbing as much as 7.5 times their weight of oil and still act as an anti-caking agent in products. This permits the ground rice hulls to be blended with various "Omega 3" or flavor compounds that are oils and the resulting powder to remain flowable. In addition, it has been observed that the ground rice hulls add a degree of stability to these otherwise fishy smelling products during further processing such as extrusion, baking, heating, etc.

The ground rice hulls are also capable of absorbing up to 2.5 times their weight of water while remaining active as anti-caking agents in products. This property is of interest to flavor companies that want to load a water based flavor on a powder, and still have a powder that flows easily. Oil based flavors may be similarly absorbed. As a further application example, a water based flavor may be applied to ground rice hulls with a moisture content of 8-10% and the flavor allowed to flow deeply into the particles. Subsequently, the particles may be dried to a low moisture content with the volatiles of the flavor binding more tightly to the substrate due to adhesion, binding and absorption thus flavor plating the substrate.

Figure 3:
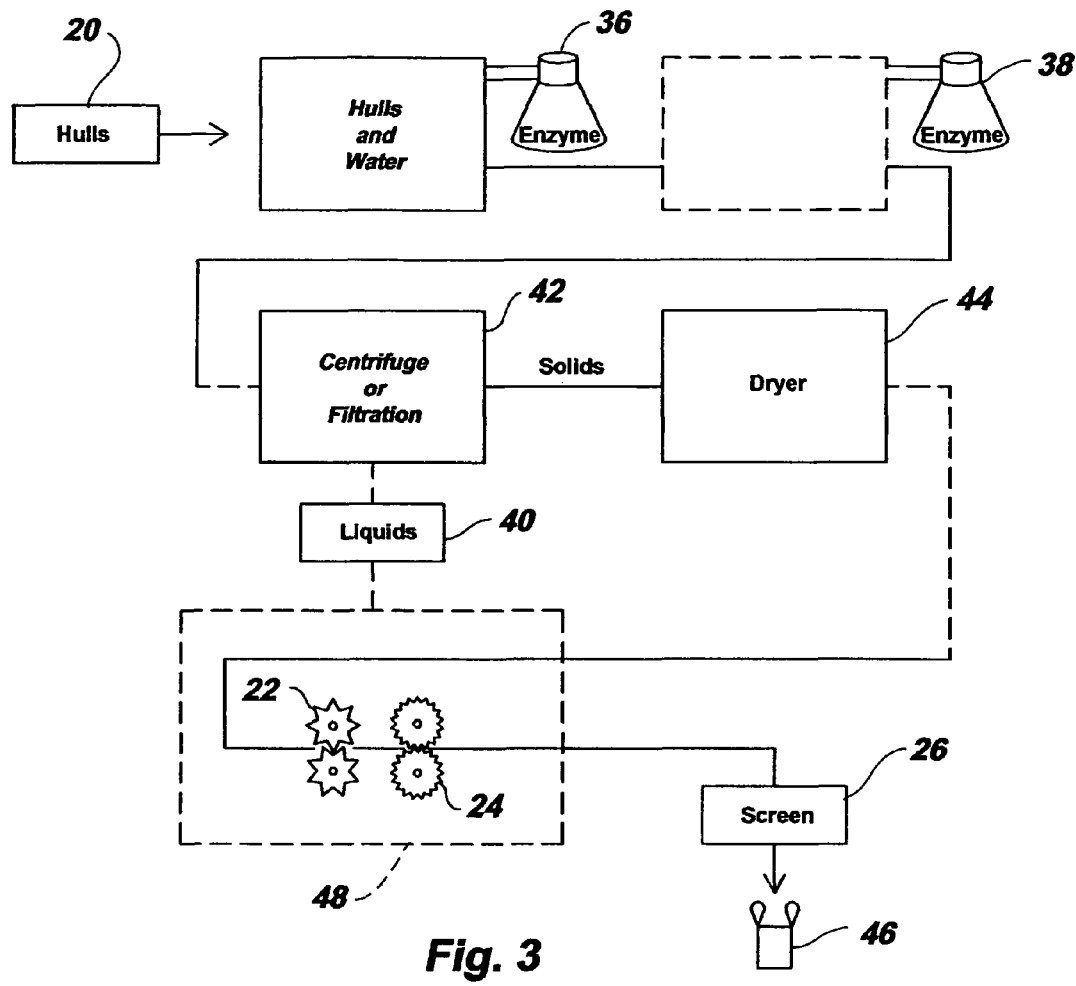
FIG. 3 is a schematic process diagram showing conversion of rice hulls into a silica-enriched product by enzymatic treatment for use as an anti-caking agent, excipient or flavor carrier in accordance with the present invention; and, FIG. 4 is a schematic process diagram showing conversion of rice hulls into a silica-enriched product by burning for use as an anti-caking agent, excipient or flavor carrier in accordance with the present invention.
Figure 4:
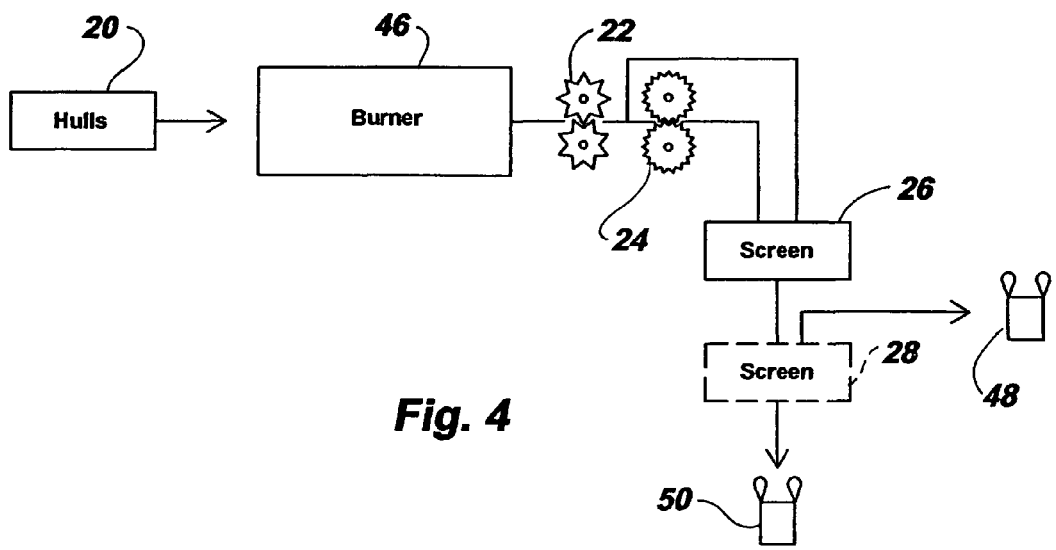

In other instances, it may be desirable to isolate or concentrate the amount of silica by reducing the amount of organic material rice hulls 20. This may be accomplished by enzyme treatment as shown in FIG. 3 or by burning as shown in FIG. 4. Turning first to FIG. 3, an enzyme 36 that digests carbon-containing compounds may be added to rice hulls 20 under proper conditions of pH, temperature and moisture. If it is desirable to remove protein also, an enzyme 38 that digests protein-containing compounds may also be added to the rice hulls 20 in the proper mixture. The enzymatic treatments may be concurrent or sequential. During digestion, the carbon-containing and protein-containing compounds are broken down into soluble products which go into solution in the water phase. After digestion is complete or has progressed by the desired amount, liquid phase 40 is separated from the solids containing biogenic silica by filtration or centrifugation 42. The solids are then dried 44 and ground and screened as described in FIG. 2 to produce a silica-concentrated rice hull product 46. Alternatively grinding step 48 may be relocated in the process such that rice hulls 20 are ground prior to enzyme treatment. Grinding step 48 may also be done on the solids before they are dried 44. It will also be understood, that antimicrobial treatment 34 as shown in FIG. 2 may be included in the process.

Turning now to FIG. 4, the carbon content of rice hulls 20 may be reduced by combustion in a burner 46. The ash remaining after combustion may be washed and then dried. The ash may then be ground as described in FIG. 1 and screened. Alternatively, the washed ash may be wet milled prior to drying and then further ground, if necessary, and screened to produce one or two products 48, 50. If desired products 48, 50 may be heated to a temperature sufficient (e.g., about 1000° C.) to convert the biogenic amorphous silica into crystalline silica. This material may also be certified as "organic" if the rice hulls or other plant material from which it is isolated are certified as organic for use as food. If desired, rice hulls 20 prior to burning or the ash after the hulls are burned may be leached with an acid such as hydrochloric, sulfuric, nitric or the like to remove minerals other than silica.

EXAMPLE

A sample of rice hulls ground as described in connection with FIG. 1 to 50 microns was submitted for analysis. On analysis, the ground rice hulls were found to contain 7.92% moisture at assay, 133° C., 7.81% protein Kjeldahl (N×6.25), 2.51% fat and 17.7% ash after treatment at 600° C. Percentages are by weight.

A portion of the ground rice hulls was also analyzed for microbial content. The results were as follows: *E. coli*: MPN/g (less than 3); *Salmonella* per 25 g (negative); and Coliforms: MPN/g ($1.1 \times 10^3$). The aerobic plate count was $6.9 \times 10^5$ cfu/g.

The results reported above may not be the same for all methods of processing.

In view of the above, it will be seen that the several objects of the invention are achieved and other advantageous results attained. As various changes could be made in the above methods and formulations without departing from the scope of the invention, it is intended that all matter contained in the above description or shown in the accompanying drawings shall be interpreted as illustrative and not in a limiting sense.

What is claimed:

1. A human or animal food product containing no synthetic amorphous silica and comprising 2% by weight or less raw rice hulls containing from 15 to 23% by weight amorphous silica in the outer layers of the rice hulls, said an amount of said rice hulls is effective as an anti-caking agent, excipient or a flavor carrier at a usage level substantially the same as synthetic amorphous silica for the same function as an anti-caking agent, excipient or a flavor carrier.

2. The formulation of claim 1 wherein the rice hulls are certified organic.

3. The formulation of claim 1 wherein the rice hulls are subjected to antimicrobial treatment before it is combined with the food product.

4. The formulation of claim 1 wherein the rice hulls have a moisture content equal to or less than 3% by weight compounded with the human or animal food, product.

\* \* \* \* \*